United States Patent [19]

Lipinski

[11] Patent Number: 4,766,141

[45] Date of Patent: Aug. 23, 1988

[54] SPIRO-SUCCINIMIDES FOR TREATMENT OF DIABETES COMPLICATIONS

[75] Inventor: Christopher A. Lipinski, New London, Conn.

[73] Assignee: Pfizer Inc., New York, N.Y.

[21] Appl. No.: 106,943

[22] Filed: Oct. 14, 1987

Related U.S. Application Data

[63] Continuation of Ser. No. 946,686, Jan. 6, 1987, abandoned, which is a continuation of Ser. No. 772,781, Sep. 5, 1985, abandoned, which is a continuation-in-part of Ser. No. 535,444, Sep. 23, 1983, abandoned.

[51] Int. Cl.[4] .................. C07D 209/96; A61K 31/40; C07B 43/08; C07B 43/06
[52] U.S. Cl. .................................. 514/409; 548/411; 558/341; 558/406; 560/82
[58] Field of Search ....................... 548/411; 514/409

[56] References Cited

U.S. PATENT DOCUMENTS

| | | | |
|---|---|---|---|
| 3,821,383 | 6/1974 | Sestanj et al. | 424/258 |
| 3,901,916 | 8/1975 | Bastian et al. | 260/326.38 |
| 3,985,888 | 10/1976 | Carr et al. | 424/267 |
| 4,117,230 | 9/1978 | Sarges | 548/309 |

FOREIGN PATENT DOCUMENTS 0065392 11/1982 European Pat. Off. .

*Primary Examiner*—Mark L. Berch
*Attorney, Agent, or Firm*—Peter C. Richardson; Lawrence C. Akers; Robert F. Sheyka

[57] ABSTRACT

Spiro-succinimides are disclosed which are useful as aldose reductase inhibitors and as therapeutic agents for the treatment of complications arising from diabetes. Pharmaceutical compositions containing the spiro-compounds and a method of treating diabetic complications are also disclosed.

12 Claims, No Drawings

SPIRO-SUCCINIMIDES FOR TREATMENT OF DIABETES COMPLICATIONS

CROSS REFERENCE TO RELATED APPLICATION

This is a continuation of application Ser. No. 946,686 filed on Jan. 6, 1987, abandoned, which is a continuation of application Ser. No. 772,781, filed on Sept. 8, 1985, abandoned, which application is a continuation-in-part of co-pending application Ser. No. 535,444, filed Sept. 23, 1983, abandoned.

BACKGROUND OF THE INVENTION

This invention relates to novel spiro-succinimides useful in the treatment of certain chronic complications arising from diabetes mellitus, such as diabetic cataracts, retinopathy and neuropathy, to pharmaceutical compositions containing such compounds and to a method of using these compounds.

In the past, various attempts have been made to obtain more effective oral anti-diabetic gents. Generally, these efforts have involved synthesis of new organic compounds, particularly sulfonylureas, and the determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. U.S. Pat. No. 4,117,230 teaches the use of certain hydantoins as aldose reductase inhibitors for treating chronic complications of diabetes. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way, unwanted accumulations of galactitol in the lens of galactosemic subjects and of sorbitol in the lens, peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

A. E. Carr et al. in U.S. Pat. No. 3,985,888 teaches certain spiroalkanone-imides and their use as sedatives. European patent application Publication No. 0065392 discloses certain spiro-succinimide derivatives and their use as aldose reductase inhibitors.

SUMMARY OF THE INVENTION

The compounds of the present invention are spiro-succinimides of the formula:

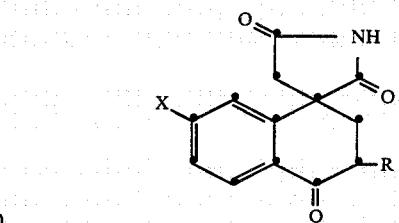

or a pharmaceutically acceptable salt thereof, wherein R is methyl or ethyl and X is fluoro or chloro.

A preferred compound is one wherein R is methyl and X is fluoro.

Both mixtures of optically active isomers and partially or completely optically resolved isomers of the compounds claimed herein are within the scope of the present invention. In particular, the present invention includes a compound of the formula:

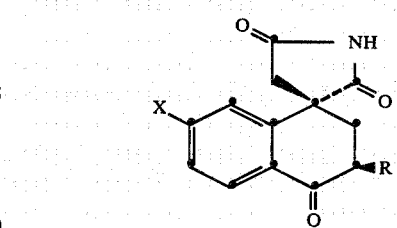

or a pharmaceutically acceptable salt thereof, wherein R and X are as defined for compounds of formula I.

A preferred compound is one wherein R is methyl and X is fluoro. Also embraced by the present invention are pharmaceutical compositions comprising a pharmaceutically acceptable carrier or diluent and a compound of formula I or II.

The present invention further comprises a method of treating a diabetic host for diabetes-associated chronic complications, which comprise administering to the host an effective amount of a compound of formula I or II.

DETAILED DESCRIPTION

The numbering system of the spiro-compounds of formula I or II is as shown below:

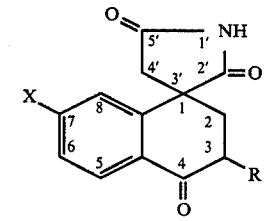

These compounds are 7-X-3-R-2,3-dihydro-spiro[naphthalene-1(4H),3'-pyrrolidine]-2',4,5'-triones.

Compounds of formula I or II can be prepared by the general method disclosed by J. M. Bastian et al. in U.S. Pat. No. 3,901,916.

According to the Bastian et al. procedure, a benzaldehyde III is reacted with dimethyl malonate IV to form a condensation product V, which is then reacted with an aqueous alkali metal cyanide solution to obtain the phenyl cyano propionate VI.

The propionate VI is reacted with an acrylate of the formula CH₂=C(R)CO₂R' wherein R' is lower alkyl, preferably having 1-4 carbon atoms, e.g. methyl or tert.-butyl methacrylate (R is methyl) or methyl or tert.-butyl ethacrylate (R is ethyl), in a polar aprotic solvent such as dimethylformamide in the presence of an alkali metal alcoholate such as potassium tert.-butoxide at a temperature of between about 25° and 120° C., preferably about 65° C.

The resulting adduct VII is then cyclyzed by reacting with a strong acid such as sulfuric acid, hydrochloric acid and the like, preferably concentrated or aqueous sulfuric acid , at a temperature range of between about 25° and 130° C., preferably about 70°-80° C., to obtain the desired compound of formula I.

The resulting diasteromers can be separated by methods known in the art such as recrystallization from a suitable solvent like isopropanol or trituration, for example, with an alcohol-ether solvent such as isopropanol-diethyl ether, to obtain compounds of formula II.

The terms "Rel" and "(±)" each means a 1:1 racemic mixture of the two optically active enantiomers.

SYNTHETIC SCHEME

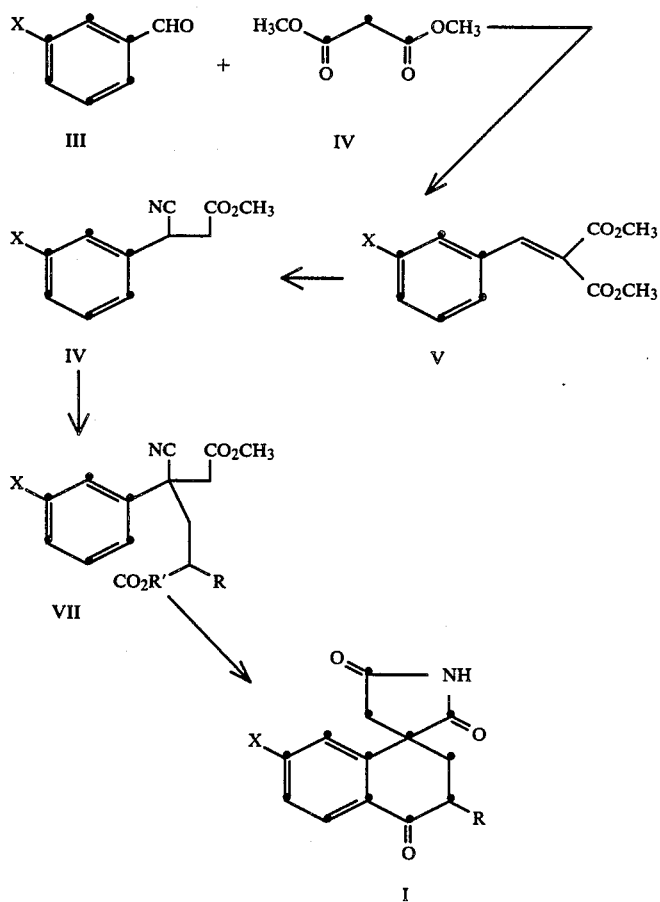

Because of the acidic hydrogen atom in the spiro heterocyclic ring of the compounds of formula I or II, salts may be formed with pharmaceutically acceptable cations by conventional methods. Thus, these salts may be readily prepared by treating the compounds of formula I or II with an aqueous solution of a base having the desired pharmaceutically acceptable cation and evaporating the resulting solution to dryness, preferably under reduced pressure. Alternatively, a lower alkanol solution of the compound of formula I may be mixed with an alkoxide of the desired cation and the resulting solution subsequently evaporated to dryness. Suitable pharmaceutically acceptable cations for this purpose include, but are not limited to, alkali metal cations such as potassium and sodium, alkaline earth metal cations such as calcium and magnesium, ammonium, lower alkanolammonium and other cations derived from pharmaceutically acceptable organic amines which form water-soluble amine addition salts.

Pharmaceutically acceptable salts are those which do not cause unacceptable adverse reactions when administered.

The novel compounds of formula I or II and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions. The compounds may be administered to a subject in need of treatment by a variety of conventional routes of administration, including orally, parenterally and topically. In general, these compounds will be administered orally or parenterally at dosages between about 0.05 and 25 mg./kg. body weight of the subject to be treated per day, preferably from about 0.1 to 10 mg./kg. per day. However, some variation in dosage will necessarily occur depending on the condition of the subject being treated. The person responsible for administration will, in any event, determine the appropriate dose for the individual subject.

The novel compounds of the invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I or II and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials this connection include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compounds of formula I or II in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Compounds of formula I or II may not only be advantageously employed for the preparation of aqueous pharmaceutical compositions for parenteral administration, as described above, but more particularly for the preparation of pharmaceutical compositions suitable for use as ophthalmic solutions. Such ophthalmic solutions are of prinicipal interest for the treatment of diabetic cataracts by topical administration and the treatment of such conditions in this manner is a preferred embodiment of the present invention. Thus, for the treatment of diabetic cataracts, the compounds of this invention are administered to the eye of the subject in need of treatment in the form of an ophthalmic preparation prepared in accordance with conventional pharmaceutical practice, e.g. see "Remington's Pharmaceutical Sciences", 15th Edition, pages 1488 to 1501 (Mack Publishing Co., Easton, Pa.). The ophthalmic preparation will contain a compound of formula I, II or a pharmaceutically acceptable salt thereof in a concentration from about 0.01 to about 1% by weight, preferably from about 0.05 to about 0.5%, in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, e.g., preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 and 8, preferably between about 7 and 7.5. Suitably tonicity agents are dextran 40, dextran 70, dextrose, glycerin, potassium chloride, propylene glycol, sodium chloride, and the like, such that the sodium chloride equivalent of the opthalmic solution is in the range of 0.9% plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, e.g., in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e., diabetic, rats; (3) measuring their ability to reverse already-elevated sorbitol levels in the sciatic nerve and lens of chronic streptozotocin-induced diabetic rats; (4) measuring their ability to prevent or inhibit galactitol formation in the lens of autely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their abiilty to reduce already elevated sorbitol levels in isolated rat lens incubated with glucose.

The present invention is illustrated by the following preparation and examples. It will be understood, however, that the invention is not limited to the specific details of these examples. Proton nuclear magnetic resonance spectra (NMR) were measured at 250 MHz (unless otherwise indicated) for solutions in per-deuterodimethyl sulfoxide (DMSO-d$_6$) and peak positions are expressed in parts per million (ppm) downfield from tetramethylsilane. The peak shapes are denoted as follows: s, singlet; d, doublet; t, triplet; q, quartet; m, multiplet; b, broad.

PREPARATION

5-Carboxy-3-cyano-3-(3-fluorophenyl)-5-methylhexanoic acid, dimethyl ester 18.66 g. (0.09 mol) of 3-cyano-3-(3-fluorophenyl)propionic acid methyl ester (prepared according to the general procedure described in U.S. Pat. No. 3,901,916—column 10) was combined with 9.33 g. (0.093 mol) of methyl methacrylate, 670 mg. (0.006 mol) of potassium tert.-butoxide and 90 ml. of dry dimethylformamide and heated at 65° C. for 21 hours. The reaction mixture was poured onto dilute hydrochloric acid solution and then was extracted with three-30 ml. portions of ethyl acetate. The ethyl acetate was concentrated to 400 ml., washed with two-300 ml. portions of water, 200 ml. of brine and dried over anhydrous sodium sulfate and concentrated to give 27.76 g. of crude oil containing the title compound. NMR 60MHZ (CDCl$_3$)δ1.12 (d of d, J=8HZ), 1.04 (d of d, J=8HZ) ppm, corresponding to a 60:40 mixture of diasteromers.

EXAMPLE 1

Rel 1,3′S,3R Spiro[naphthalene-1(4H), 3′-pyrrolidine]-2′, 4,5′-trione-2,3-dihydro-7-fluoro-3-methyl A. 12.5 g. of crude 5-carboxy-3-cyano-3-(3-fluorophenyl)-5-methylhexanoic acid dimethyl ester was combined with 62.5 ml. of concentrated sulfuric acid and was heated at 70° C. for 2.5 hours. The reaction was quenched over ice and extracted with three-100 ml. portions of ethyl acetate. The ethyl acetate solution was extracted with pH 11 aqueous sodium hydroxide. The aqueous base layer was washed with ethyl acetate, and the aqueous layer was adjusted to pH 2 with hydrochloric acid and extracted with four-100 ml. portions of ethyl acetate. After drying over anhydrous sodium sulfate, the ethyl acetate extract was concentrated in vacuo to an oil and eventually to a white foam. This was triturated for 20 hours with isopropyl alcohol-diethyl ether to give, after drying at 110° C. at reduced pressure, 610 mg. of the title compound, m.p. 200°–202° C. (shrinks), 212°–215° C. (decomp.). Anal. (C$_{14}$H$_{12}$O$_3$NF). Calcd. C,64.36; H,4.63; N,5.36. Found: C,64.25; H,4.60; N,5.42. IR(KBr): 3228, 1723, 1705, 1692, 1605, 1343, 1236, 1199, 1186 cm$^{-1}$. NMR 250 MHZ (CD$_3$SOCD$_3$): δ11.7 (vbs, 1, NH), 7.97(m, 1), 7.31(m, 1), 7.13(m, 1), 3.5-2.1(m, 5), and 1.16(d, 3) ppm. Peaks attributable to a minor diasteromer (major/minor ratio=9) were observed at 7.47 ppm (aromatic H) and 1.12 ppm (one of two peaks of CH$_3$ doublet). Decoupling of the methyl group protons sharpens the resonance of the keto carbonyl signal, but does not affect either of the imido carbonyl groups. This experiment defines the structure of the major diasteromer as the title spiro[naphthalene pyrrolidine]trione rather than the alternate indanone spiro-methyl glutarimide cyclization product. Tritration of the product with 0.5 N sodium hydroxide gave a pkA value of 9.59 in 1:1 dioxane-water and 8.25 in water, values which are consistent with a succinimide but not with a glutarimide.

B. The procedure of A was employed using an aqueous solution containing 90% sulfuric acid instead of concentrated sulfuric acid and heating at 80° C. for 1–2 hours instead of at 70° C. for 2.5 hours. The desired reaction product was isolated in 15–18% crude yield and recrystallized from isopropanol to obtain a 92:8 diasteromic mixture with the same major diastereomer as in A.

EXAMPLE 2

Rel 1,3′S,3R Spiro[naphthalene-1(4H),3′-pyrrolidine]-2′,4,5′-trione-2,3-dihydro-7-fluoro-3-methyl, the product prepared according to the procedure of Example 1B, was tested for inhibition of aldose reductase obtained from human placenta by using the procedure described by M. J. Peterson et al. in *Metabolism*, Vol. 28, No. 4, Suppl. 1, p. 456 (1979). The results obtained are expressed in terms of the percent inhibition of aldose reductase enzyme activity (i.e., relative to the aldose activity in the absence of inhibitor) afforded by the compound at three different molar concentration levels (viz., $10^{-5}$, $10^{-6}$ and $10^{-7}$M). In this way, it was found that the title compound of Example 1 affords a 78% inhibition value at $10^{-5}$M, a 41% inhibition value at $10^{-6}$ and a 3% inhibition value at $10^{-7}$ M, respectively.

EXAMPLE 3

Rel 1,3′S,3R Spiro[naphthalene-1(4H),3′-pyrrolidine]-2′, 4,5′-trione-2,3-dihydro-7-fluoro-3-methyl, the product prepared according to the procedure of Example 1B, was tested for its ability to reduce or inhibit sorbitol accumulation in the sciatic nerve and lens of diabetic rats. This was done by following the procedure described by M. J. Peterson et al. in *Metabolism*, Vol. 28, No. 4, Suppl. 1, p. 456 (1979). A single intravenous dose of streptozotocin (85 mg./kg.) was administered to rats. The test compound was fed to the rats orally at four, seven and 24 hours after the administration of the streptozotocin. At 27 hours after streptozotocin administration, the animals were sacrificed and the sciatic nerve and lens were both removed for sorbitol assay. The control animals were given the same streptozotocin treatment, but were not given the test compound. The results obtained are expressed in terms of percent inhibition of sorbitol (i.e., relative to the control) afforded by the test compound in both the sciatic nerve and lens at three different dosage levels tested (viz., 2.5, 1.5 and 1.0 mg./kg.). In this way, it was found that the title compound of Example 1 affords a 75% inhibition value in the sciatic nerve when tested at 25 mg./kg., a 76% inhibition value at 1.5 mg./kg. and a 69% value at 1.0 mg./kg.; the corresponding values in the lens wre 56%, 39% and 39%, respectively.

I claim:

1. A compound of the formula:

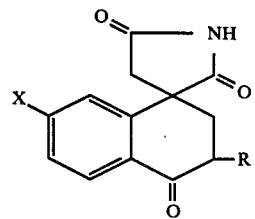

or a pharmaceutically acceptable salt thereof, wherein:
R is methyl or ethyl; and
X is fluoro.

2. A compound according to claim 1 wherein R is methyl and X is fluoro.

3. A pharmaceutical composition comprising a compound according to claim 1 in an amount effective for the treatment of chronic diabetic complications and a pharmaceutically acceptable carrier or diluent.

4. A pharmaceutical composition according to claim 3 wherein R is methyl and X is fluoro.

5. A method for treating chronic diabetic complications in a mammal, which comprises administering to said mammal an effective amount of a compound according to claim 1 in combination with a pharmaceutically acceptable carrier or diluent.

6. A method according to claim 5 wherein R is methyl and X is fluoro.

7. A compound of the formula:

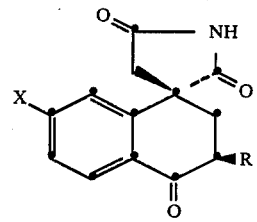

or a pharmaceutically acceptable salt thereof, wherein:
R is methyl or ethyl; and
X is fluoro.

8. A compound according to claim 7 wherein R is methyl and X is fluoro.

9. A pharmaceutical composition comprising a compound according to claim 7 in an amount effective for the treatment of chronic diabetic complications and a pharmaceutically acceptable carrier or diluent.

10. A pharmaceutical composition according to claim 9 wherein R is methyl and X is fluoro.

11. A method for treating chronic diabetic complications in a mammal, which comprises administering to said mammal an effective amount of a compound according to claim 7 in combination with a pharmaceutically acceptable carrier or diluent.

12. A method according to claim 11 wherein R is methyl and X is fluoro.

* * * * *